US006488653B1

(12) United States Patent
Lombardo

(10) Patent No.: US 6,488,653 B1
(45) Date of Patent: Dec. 3, 2002

(54) DILATION BALLOON HAVING MULTIPLE DIAMETERS

(75) Inventor: Giuseppe Lombardo, Largo, FL (US)

(73) Assignee: Wilson-Cook Medical Incorporated, Winston-Salem, NC (US)

( * ) Notice: Subject to any disclaimer, the term of this patent is extended or adjusted under 35 U.S.C. 154(b) by 110 days.

(21) Appl. No.: 09/636,442

(22) Filed: Aug. 11, 2000

Related U.S. Application Data
(60) Provisional application No. 60/148,529, filed on Aug. 12, 1999.

(51) Int. Cl.[7] .............................................. A61M 29/00
(52) U.S. Cl. ............................ 604/103.06; 604/101.01; 606/194
(58) Field of Search ......................... 604/96.01, 101.01, 604/101.05, 103.06, 103.07; 606/192, 194

(56) References Cited

U.S. PATENT DOCUMENTS

| | | | |
|---|---|---|---|
| 3,970,090 A | | 7/1976 | Loiacono |
| 4,958,634 A | | 9/1990 | Jang |
| 4,990,139 A | | 2/1991 | Jang |
| 5,019,042 A | * | 5/1991 | Sahota ................... 604/103.06 |
| 5,269,758 A | * | 12/1993 | Taheri ..................... 604/96.01 |
| 5,273,536 A | | 12/1993 | Savas |
| 5,308,356 A | * | 5/1994 | Blackshear, Jr. et al. ... 606/194 |
| 5,338,298 A | | 8/1994 | McIntyre |
| 5,411,016 A | | 5/1995 | Kume et al. |
| 5,620,457 A | * | 4/1997 | Pinchasik et al. ........... 606/194 |
| 5,681,344 A | | 10/1997 | Kelly |
| 5,711,754 A | | 1/1998 | Miyata et al. |
| 5,843,116 A | | 12/1998 | Crocker et al. |
| 6,022,359 A | * | 8/2000 | Frantzen .................. 604/96.01 |

FOREIGN PATENT DOCUMENTS

WO    9929370    6/1999

OTHER PUBLICATIONS http://www.bardinterventional.com/dilat.htm; BARD Interventional Products Division; Jul. 1, 1999.
http://www.bsci.com/divisions/endoscopyTech.html; Microvasive Endoscopy; CRE™ Wireguided; Nov. 7, 2000.
Premarket Notification, CRE™ Balloon Dilatation Catheter, Apr. 7, 1997.

* cited by examiner

Primary Examiner—Ronald Capossela
(74) Attorney, Agent, or Firm—Brinks Hofer Gilson & Lione

(57) ABSTRACT

A dilation balloon catheter is disclosed comprising a non-compliant balloon attached to a catheter, the balloon portion includes a plurality of sections having different outer diameters, as measured at the central portion or midpoint of the section, when the balloon is inflated. In one embodiment that is deployable from an endoscope to treat esophageal, pyloric, or colonic strictures, a series of progressively larger balloon sections are used to safely dilate the stricture in stages. Each section includes a central portion having a waist for centering the balloon over the stricture, with the distal section having the smallest diameter and the intermediate and proximal sections being about 2 and 4 mm larger, respectively. A wire guide extends throughout the length of the catheter and balloon and forms a distal portion of the dilation balloon catheter for assisting in cannulation of the stricture. Optionally, the dilation balloon catheter can include a series of bands or other markings to indicate the location of the different balloon sections. These indicia can be located on the wire guide or the balloon material and may be radiopaque.

22 Claims, 3 Drawing Sheets

DILATION BALLOON HAVING MULTIPLE DIAMETERS

RELATED APPLICATION

This application claims priority of Provisional Patent Application No. 60/148,529 filed Aug. 12, 1999 in the United States Patent Office.

TECHNICAL FIELD

This invention relates generally to surgical devices, and more particularly to catheters, dilators and other devices for establishing, restoring or enlarging lumens in the body, especially in the intestines and esophagus.

BACKGROUND OF THE INVENTION

A variety of body lumens are subject to undesired strictures or narrow regions. For example, blood vessels can be blocked or narrowed by atherosclerosis, while esophageal strictures can arise from individual anatomical differences, or from diseases such as connective tissue disorder. Procedures for dilating or enlarging such strictures or narrowed regions often entail the use of a balloon dilation catheter. Such catheters include a deflated balloon which can be positioned across a particular stricture or narrowed region, and which is then inflated with a fluid in order to widen the lumen without trauma to the wall of the lumen.

A variety of balloon catheters and dilators are known which include a balloon attached to the distal end of a catheter tube or shaft, and which also include a stainless steel or nitinol wire stiffener extending through the catheter shaft and balloon. Balloons for dilating esophageal, pyloric, or colonic strictures can be made of a semi- or non-compliant material that permits sufficient expansile force to dilate the stricture. Non-compliant materials, such as polyethylene terephthalate (PET), are preferred over semi-compliant or compliant materials because they are much less prone to "dog boning", a situation in which the resistance of the stricture forces the fluid in the balloon to either side, therefore providing comparatively less radial or expansile force than would a standard non-compliant balloon.

While dilation of stenoses in blood vessels is usually performed as a one step procedure, there is often a clinical advantage in being able to dilate esophageal and other gastrointestinal strictures using a series of progressively larger balloons so as to avoid tearing or perforation of the luminal wall. The disadvantage of sequentially introducing larger balloons is that multiple introductions increase risk to the patient and prolongs the procedure. One factor determining the length of the procedure is the difficulty in being able to precisely position and reposition the balloon at the stricture. Additionally, patient discomfort is naturally a concern when multiple catheter introductions are required. What is needed is a dilation balloon that can efficiently and effectively perform staged dilation of a stricture while minimizing risk and discomfort to the patient.

SUMMARY OF THE INVENTION

The foregoing problems are solved and a technical advance is achieved in an illustrative dilation balloon catheter comprising a single non-compliant balloon, made of polyethylene terephthalate (PET) or another suitable material, that is formed, such as over a mold, to include a plurality of longitudinal sections, each having a different diameter at the center of the section. The balloon can be attached to the distal end of a catheter made of a polymer, such as polyurethane, using a bonding means such as a UV adhesive. In one embodiment used in conjunction with an endoscope to dilate esophageal, colonic, and pyloric strictures, the dilation balloon comprises three sections with the distal section having the smallest diameter. A wire guide, e.g., of a nitinol (NiTi) alloy, can extend through the lumen of the catheter, the balloon, and extend distally, encased in a protective polymer jacket, to aid in cannulation of the stricture.

To cannulate a stricture of a body lumen such as the esophagus, the balloon portion is advanced from the endoscope and the stricture is dilated using the distal (smallest) section. The balloon is usually deflated, then the second, intermediate section, which is about 2 mm larger that the first, is advanced over the stricture and inflated. Finally, the proximal section, which is yet another 2 mm larger, can be used to make a third dilation of the stricture, if desired, before the balloon catheter is removed from the patient. This staged series of inflation helps avoid tearing or perforating of the particular body lumen being dilated, while the single balloon allows a single introduction into the patient for the procedure, rather than requiring three separate introductions of different-sized balloons. In addition, the single balloon can be attached to a smaller diameter catheter, since it is does not have to be multi-lumen, an important advantage when being used in endoscopy.

In one aspect of the invention, the central portion of each balloon section is depressed to form a waist that helps the balloon to center itself over the stricture. This waist, normally 2–6 mm narrower than the adjacent portions of the section, can be configured to include an abrupt change in diameter, creating somewhat of a dumbbell-shaped balloon section, or it may be more gradual in transition. In an illustrative embodiment of a three section balloon, the adjacent portions of the intermediate section are basically shared with the distal adjacent portion of proximal section and the proximal adjacent portion of the distal section, respectively. The number of sections is determined by the number of different central portions or waists of the balloon, rather than the number of adjacent portions, which are often going to be one greater in number than the central portions.

In another aspect of the invention, the longitudinal positions of the different balloon sections can be marked with indicia that can be observed under fluoroscopic imaging and/or via the endoscope. The indicia can be imprinted on, or incorporated into the wire guide that extends through the balloon, using ink, bands, or other means. Additionally, the indicia can be directly printed on, or applied to the balloon surface (e.g., using thin radiopaque foil). The indicia, which preferably marks the center of the balloon section, can be different for each balloon section, or it can be the same.

BRIEF DESCRIPTION OF THE DRAWING

Embodiments of the present invention will now be described by way of example with reference to the accompanying drawings, in which.

DETAILED DESCRIPTION

Figure 1:
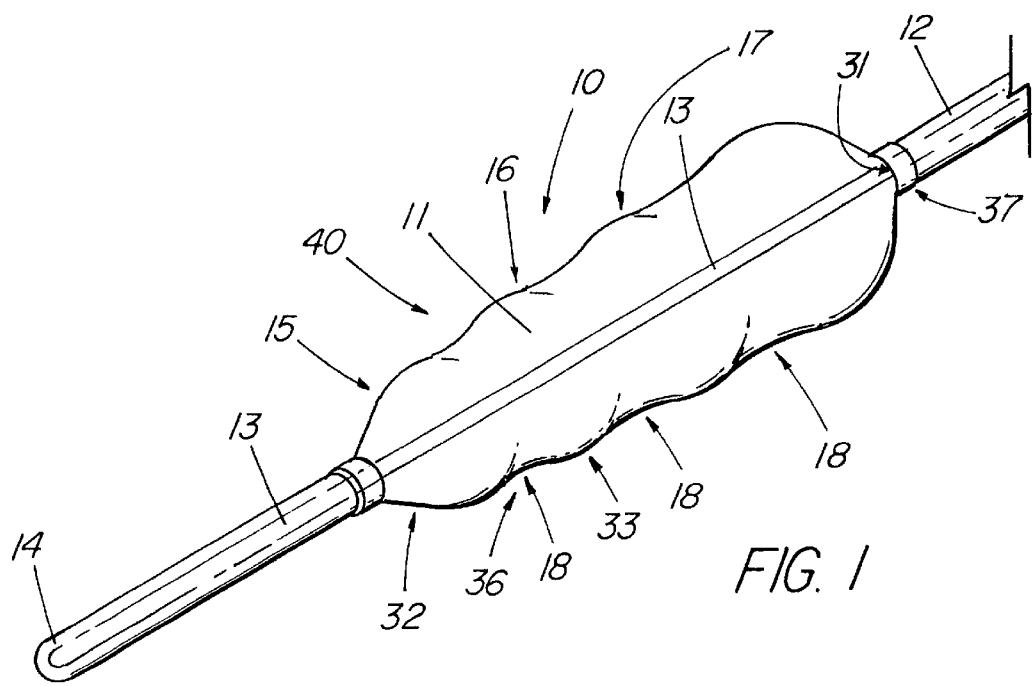
FIG. 1 depicts a pictorial view of the illustrative embodiment of the present invention.

FIG. 1 depicts a pictorial view of the illustrative embodiment of the present invention of a dilation balloon catheter 10 comprising a single non-compliant balloon 11 mounted distally to a catheter 12 with a lumen 31 extending therethrough that also contains a wire guide 13 which extends the length of the balloon 11. The lumen 31 of the catheter 12 serves as the inflation lumen for the balloon 11, which is normally filled with saline or water to a pressure of 40–100 psi (about 275–690 kPa), typically about 60 psi (413 kPa). The wire guide 13 extends beyond the balloon 11 to form a distal portion 14 that facilitates cannulation of a stricture for placement of the balloon. The balloon 11 is longitudinally divided into three sections 15,16,17, each having a different maximum outer diameter when inflated and each in communication with one another. Naturally, it is within the scope of this invention to have any number of different diameter sections from two up to as many as is practical for a given procedure. It is also within the scope of the invention to have one or more additional balloons, separate from the multiple-section balloon, that can be separately inflated via a different lumen, and possibly be of a different shape, diameter, or material than that of the primary balloon of the present invention. In the illustrative embodiment, the first diameter section 15, comprising approximately the distal one-third of the balloon, has the smallest diameter. The second diameter section 16 and third diameter section 17 comprising the middle and proximal portions, respectively, of balloon 11, are progressively larger in diameter. In the illustrative balloon 10, which is used for dilating esophageal, pyloric, or intestinal strictures, the respective sections 15,16,17 of balloon 11 have diameters of 18, 16, and 14 mm as measured from the midpoint or central portion 36 of each section, with the range for balloon sections appropriate for particular these anatomical sites being generally within the 4 to 25 mm range. The typical balloon length for esophageal use would be about 8 cm, while a 5.5 cm length would be appropriate for colonic and pyloric dilation.

In the illustrative embodiment of FIG. 1, the balloon is made of non-compliant material such as polyethylene terephthalate (PET), irradiated polyethylene, or nylon. For the use described, the thickness of the material should ideally fall within the range of 0.005 to 0.02" (0.13 to 0.5 mm) to provide a dilation balloon that will exert sufficient force against the luminal wall without causing rupture, yet still fit within the channel of an endoscope. The balloon of the illustrative embodiment can be formed using well-known techniques. One method includes heating a tube of PET, then stretching and inflating the material within a mold to create the desired final shape. For example, a tube having an O.D. of 0.150" (3.8 mm) and a wall thickness of 0.008" to 0.015" (0.2 to 0.38 mm) can be used to produce a 14–16–18 mm diameter balloon. After convection heating of a central portion of the tube for about 15–45 seconds, the heat source is retracted and a mold of the fully distended shape of the balloon is placed over the tube. The tube is stretched along its longitudinal axis to create a thin-walled portion corresponding to the final length of the balloon. At that point, pressurized gas is introduced through one end of the tube, the tube being sealed at the other end, thereby expanding the heated tube to conform with the inner surface of the mold. After a brief interval, the gas is partially released to a point above 1 atmosphere such that when the mold is retracted, the balloon remains inflated in its generally distended shape. After a brief cooling period the balloon is ready to be removed and bonded to the catheter. In the illustrative embodiment, the PET balloon is bonded to a catheter made of polyurethane (PELLETHANE®, Dow Corning Co.) using a UV adhesive. Other appropriate medical device adhesives can be used as well.

While the balloon of FIG. 1 includes three main section 15,16,17, each having a different nominal diameter, the sections themselves are not of a uniform diameter. To assist the balloon in centering over a stricture and maintaining its position during inflation, a depression or waist 18 is formed at the central portion 36 of each section 15,16,17. As used in the specification and claims herein, the measurements of the diameter of the balloon sections 40 as defined, are taken about the waist 18 of the central portion 36 at each section's midpoint. This value represents the nominal diameter of the balloon section with the widest point of the adjacent portions 32,33 of the section 15 being 2–6 mm greater in diameter. That difference between the two points 36 and 32 or 33, is 2 mm in the illustrative embodiment. It is the number of different central portions 36 that determine the number of sections in the balloon, not the number of adjacent portion 32,33, which in the embodiment of FIG. 1 appear a four distinct enlarged sections surrounding the three waists 18 of the respective central portions.

Figure 4:
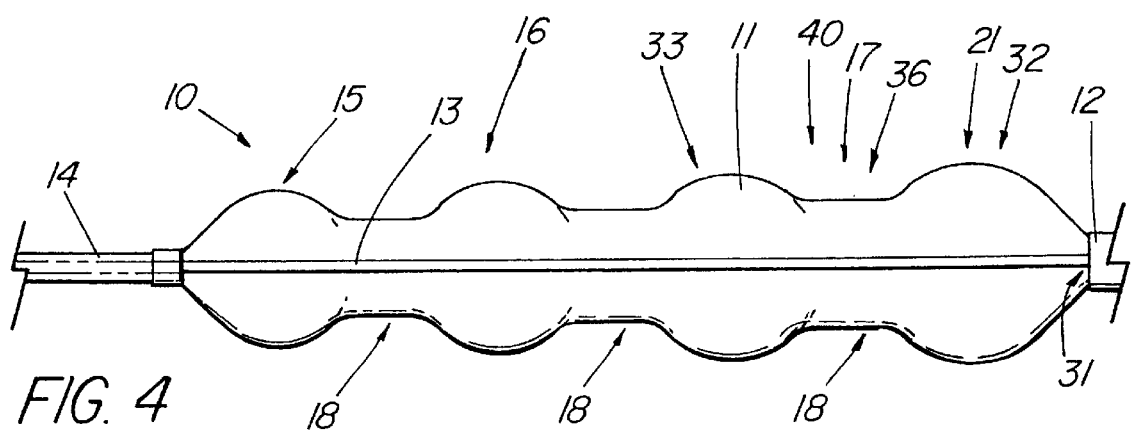
FIG. 4 depicts a side view of an alternative embodiment of the present invention.
Figure 7:
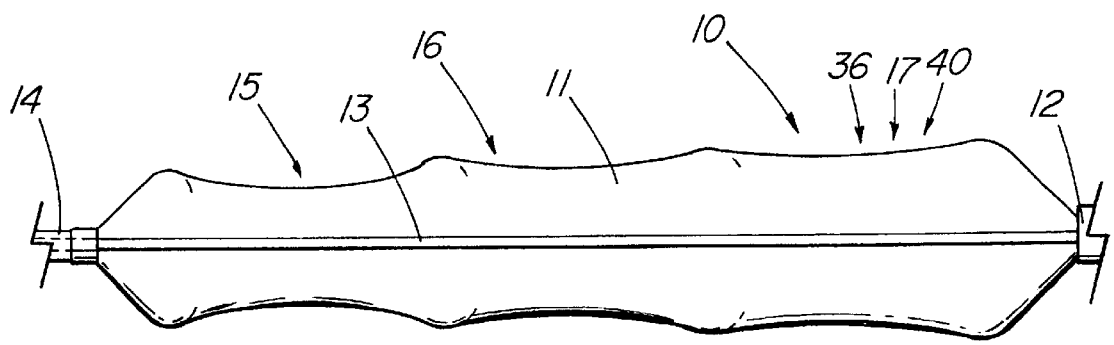
FIG. 7 depicts a side view of an embodiment of the present invention showing alternatively shaped balloon sections.

FIG. 4 depicts an alternative embodiment of the balloon in which the sections 15,16,17 of the balloon are dumbbell shaped. In this embodiment the waist 18 is more abruptly defined relative to the adjacent sections 32,33, which are more spherical in shape than in the embodiment of FIG. 1. An embodiment without a well-defined waist 18 at the central portion 36 is depicted in FIG. 7. In the this embodiment, each of the sections 40 are of substantially of the same diameter, or are only slightly concave at the center portion 36.

To provide the balloon catheter sufficient rigidity, a wire guide 13 is included within the lumen of the catheter 12 and the balloon 11. The wire guide does not completely fill the lumen such that fluid can adequately traverse the lumen to inflate the balloon. Alternatively, a multiple lumen catheter can be used with the wire guide being situated within a lumen that is separate from the inflation lumen. The preferred wire guide material is a superelastic alloy such as nitinol (NiTi alloy), although a standard stainless steel wire guide can be used. A 0.023" (0.58 mm) diameter nitinol wire guide offers good rigidity for introduction into the gastrointestinal system and to cannulate strictures, while remaining highly flexible within a tortuous navigational path. The distal portion 14 includes the distal portion of the wire guide 13 that is coated or encased in a polymer such as polyurethane. To make the distal portion 14 less traumatic to tissue, the nitinol wire guide 13 is ground to a gradual taper over the distal 5 cm of the device.

Figure 2:
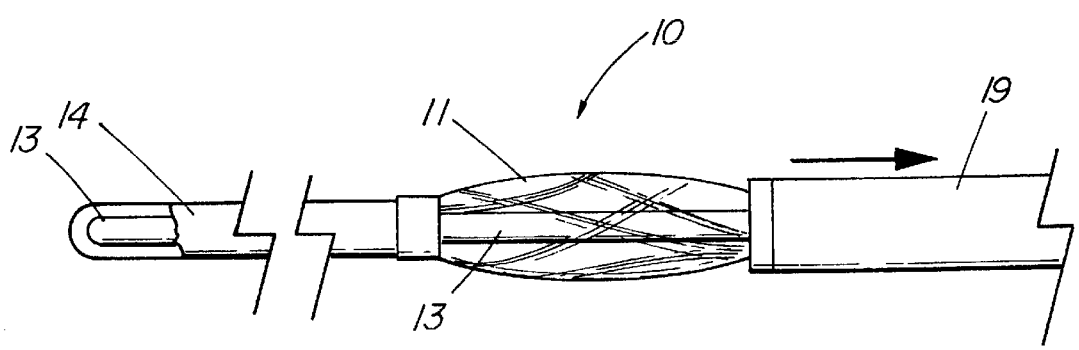
FIGS. 2–3 depict side views of an embodiment of the present invention being deployed from an endoscope.

FIG. 2 depicts deployment of the balloon catheter 10 from the accessory channel of a standard endoscope 19. The endoscope 19 serves as an outer constraining device for introducing the balloon catheter 10 to the target site. The uninflated balloon 11 is shown partially advanced from the end of the endoscope 19. When used with an endoscope, the balloon 11 is normally deployed completely before it is inflated, primarily to avoid damaging the accessory channel of the scope.

Figure 3:
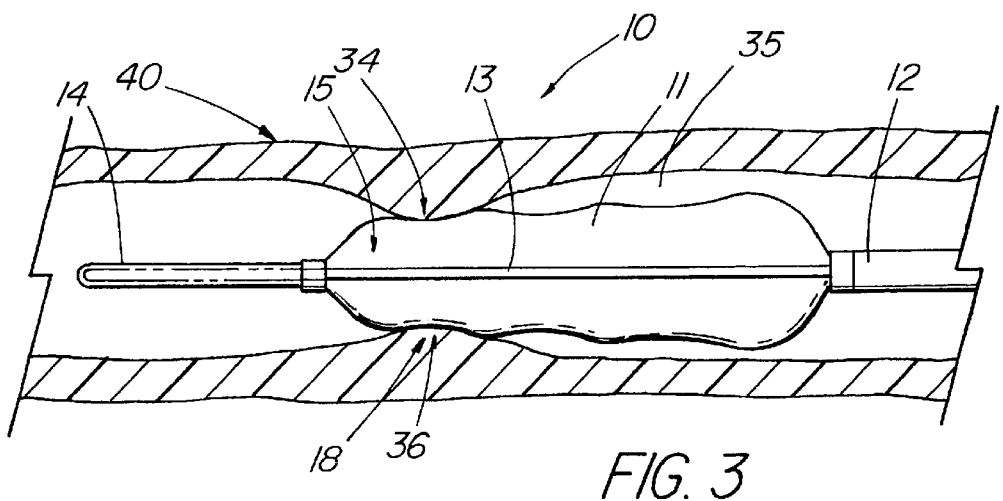

Clinical use of the dilation balloon catheter is depicted in FIG. 3. Initially, the stricture is examined and sized using the endoscope. In the illustrative example, a dilation balloon catheter 10 is selected having three sections wherein the distal section 15 (the smallest section) is sized approximately 2 mm larger than the stricture opening 34. It is clinically important when dilating many types of strictures that dilation be conducted in stages, rather attempt dilating the stricture in a single step, such as how an angioplasty procedure is performed. Gradual dilation will prevent the esophagus, colon, or other body lumen from tearing or perforating from the expansile force of the balloon. Following inspection of the stricture, the dilation balloon catheter 10 is advanced through the scope to the site of the stricture 34 and is cannulated by the distal portion 14 of the balloon catheter 10. As shown in the figure, the distal section 15 is positioned with the waist 18 over the stricture 34 and then inflated. The waist naturally centers over the narrowest part of the stricture 34 and keeps the balloon section 15 from slipping to one side or another. After dilation, the balloon 11 is then partially deflated. The middle section 16, which is 2 mm larger that the distal section, is advanced over the stricture 18 and the balloon reinflated. If desired, the proximal section 17 is used as a third dilation of the stricture. For gastrointestinal strictures, many physicians consider 6 mm (or three inflations) to be the maximum amount of dilation that can be safely performed without risking damage to the body lumen being treated. Alternatively, it would also be possible to locate the largest end of the balloon at the distal end, advance the distal 15 and/or middle 16 sections beyond the stricture 18, and initially dilate using a middle 16 or proximal 17 sections, then moving distally. The disadvantage of this is that you will possibly advance much of the balloon catheter past the stricture without the benefit of having been able to inspect this distal this distal region endoscopically, thereby adding potential risk to the procedure.

Figure 5:
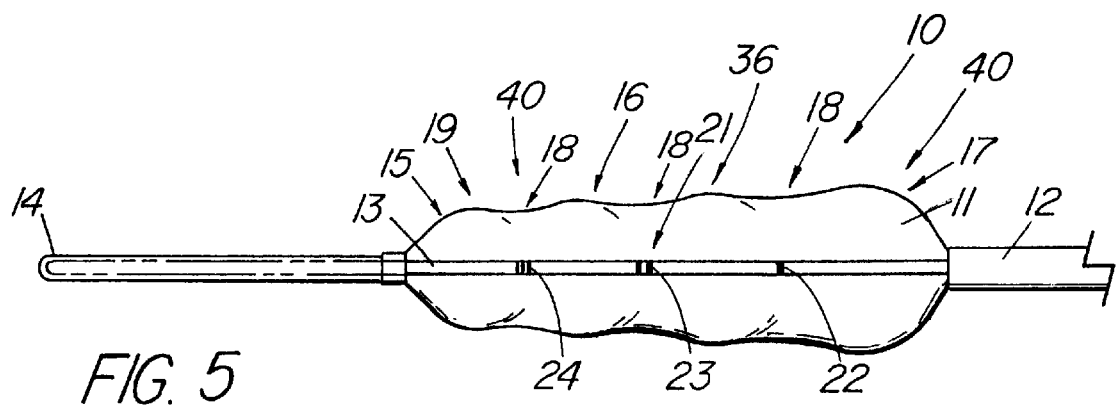
FIGS. 5–6 depict side views of alternative embodiments of the present invention having indicia to facilitate positioning of the device.
Figure 6:
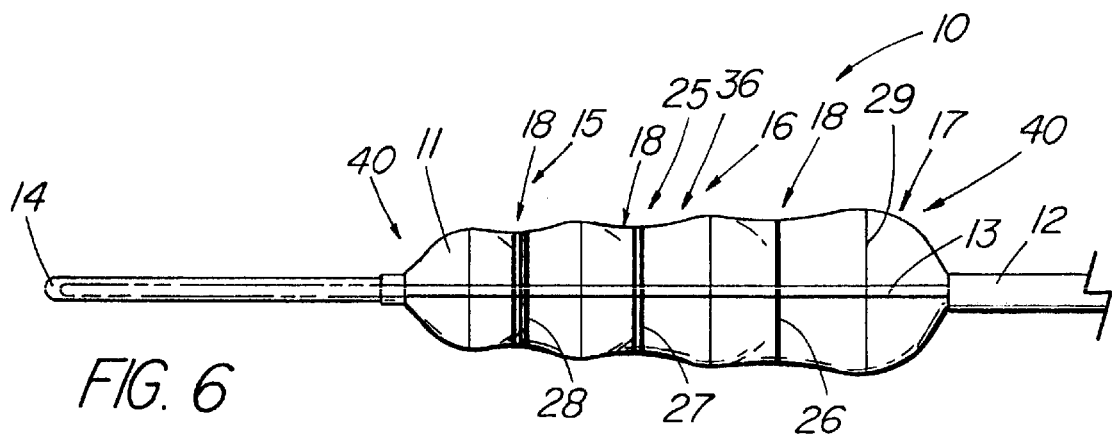

FIGS. 5–6 depict alternative embodiments of the present invention in which a system of indicia 21,25 are placed on the balloon catheter 10 to enable the clinician to orient a given section of the balloon to the stricture or other desired site, either under fluoroscopy or via direct visualization (e.g., through an endoscope). In the embodiment of FIG. 5, the series of indicia 21 are placed on the wire guide 13 for orienting the balloon 11 to the desired location. The marks are placed at each section 15,16,17 of the balloon 11 and can each be identical vary in shape, color, or number as in the illustrative example. As depicted, the first wire guide indicium 22 comprises a single band that corresponds to the center portion 36 or waist 19 of the distal balloon section 15, while the second wire guide indicium 23 comprises a double band identifying the intermediate 16 section. The third wire guide indicium 24 comprises a triple band that corresponds to the center portion 36 or waist 19 of the proximal section 17. As used herein, "indicium" is defined can include a single identifier, such as a band, dot, number, color, etc., or combination of markings (i.e., double bands, dots, etc.) that is used to designate the location of a single balloon section. These markings or indicia 21 can be made radiopaque to assist the physician in positioning the balloon under a fluoroscope. Bands or other indicia made of a material such as gold, platinum, or tantalum can be applied to the outer surface of the wire guide or metal. Other types of radiopaque materials can also be applied to or deposited on the surface of the wire, such as an ink, paint, or polymer containing barium or tantalum, etc. As an alternative to providing varying numbers of bands, dots, etc, to mark the different balloon sections, numbering or lettering can be used, especially if the purpose of the indicia is to be viewable by the endoscope.

FIG. 6 depicts an alternative embodiment having system of indicia for positioning of the balloon, comprising markings 25 that are imprinted on the balloon 11 material. Much like the embodiment of FIG. 5, a first balloon indicium 26, comprising a single stripe, encircles the balloon 11 at the waist 19 of the distal balloon section 15, while the second and third balloon indicia 27,28, comprising double and triple stripes, identify the middle and proximal balloon sections 16,17, respectively. The stripes can comprise metal particles that are deposited on the outer surface using well-known techniques. Typically, a 0.002" (0.05 mm) thick deposit with provide sufficient radiopacity. Alternatively, thin strips of a radiopaque material, such as a microthin metal foil, can be applied to the balloon, or a radiopaque material can be imprinted directly on the balloon material.

Except where the teachings differ, one can look to U.S. Pat. No. 5,681,344 to Kelly for additional details of the construction and use of an esophageal dilation balloon made of PET and having a nitinol wire guide. The balloon of the '344 patent is similar to the present invention, with the primary difference being that the Kelly balloon is of a single diameter. Any other undisclosed or incidental details of the construction or composition of the various elements of the disclosed embodiment of the present invention are not believed to be critical to the achievement of the advantages of the present invention, so long as the elements possess the strength or flexibility needed for them to perform as disclosed. The selection of these and other details of construction are believed to be well within the ability of one of even rudimentary skills in this area, in view of the present disclosure.

What is claimed is:
1. A dilation balloon catheter comprising:
a catheter having a distal end, the catheter having at least one lumen extending therethrough; and
a balloon affixed to the catheter, the balloon including a plurality of distinct balloon sections, each balloon section having a central portion and adjacent portions located on either side of the central portion, the central portion having a diameter that is smaller than a diameter of the adjacent portions, wherein the diameter of the central portion of each of the balloon sections, when the balloon is inflated, has a diameter that is different than the diameter of the central portions of the other balloon sections.
2. The balloon catheter of claim 1 wherein the balloon comprises a non-compliant material.
3. The balloon catheter of claim 2 wherein the non-compliant material includes polyethylene terephthalate.
4. The balloon catheter of claim 1 wherein the balloon catheter includes a system of indicia, wherein at least one indicium of the system of indicia corresponds with the central portion of at least one of the plurality of balloon sections.
5. The balloon catheter of claim 1 wherein the plurality of balloon sections comprises a distal section having a central portion and adjacent portions located on either side of the central portion, an intermediate section having a central portion and adjacent portions located on either side of the central portion, and a proximal section having a central portion and adjacent portions located on either side of the central portion.
6. The balloon catheter of claim 5 further comprising:
a first indicium corresponding to the central portion of the proximal section;
a second indicium corresponding to the central portion of the intermediate section; and
a third indicium corresponding to the central portion of the distal section.
7. The balloon catheter of claim 6 wherein at least one of the first indicium, second indicium, and third indicium is located about the wire guide.

8. The balloon catheter of claim 6 wherein at least one of the first indicium, second indicium, and third indicium is located about the balloon.

9. The balloon catheter of claim 6 wherein the proximal section has a first diameter, the intermediate section has a second diameter that is different from the first diameter, and the proximal section has a third diameter that is different from the first and the second diameters.

10. The balloon catheter of claim 5 wherein the first diameter is smaller than the second and the third diameters.

11. The balloon catheter of claim 1 further including a wire guide situated within one of the at least one lumen of the catheter and extending through the catheter and the balloon.

12. The balloon catheter of claim 11 wherein the wire guide comprises a superelastic alloy.

13. The balloon catheter of claim 1 wherein, when the balloon is inflated, the central portion of each balloon section has a concave outer surface with respect to a central axis of the catheter, and the adjacent portions of each balloon section has a convex outer surface with respect to the central axis of the catheter.

14. A dilation balloon catheter comprising:
   a catheter having a distal end, the catheter having a lumen extending therethrough;
   a balloon made of a non-compliant material, the balloon being affixed about the distal end of the catheter, the balloon comprising at least a distal section, an intermediate section and a proximal section, each of said distal, intermediate and proximal sections having a central portion and adjacent portions located on either side of the central portion, the central portion having a diameter that is smaller than a diameter of the adjacent portions, wherein the diameter of the respective central portions of each of the distal, intermediate and proximal sections, when the balloon is inflated, is different from the diameters of the central portions of the other sections; and
   a wire guide situated within the at least one lumen of the catheter and extending through the catheter and the balloon.

15. The balloon catheter of claim 14 further comprising:
   a first indicium corresponding to the central portion of the proximal section;
   a second indicium corresponding to the central portion of the intermediate section; and
   a third indicium corresponding to the central portion of the distal section.

16. The balloon catheter of claim 15 wherein at least one of the first indicium, second indicium, and third indicium is located about the wire guide.

17. The balloon catheter of claim 15 wherein at least one of the first indicium, second indicium, and third indicium is located about the balloon.

18. The balloon catheter of claim 16 wherein the proximal section has a first diameter, the intermediate section has a second diameter that is different from the first diameter, and the proximal section has a third diameter that is different from the first and the second diameters.

19. The balloon catheter of claim 18 wherein the first diameter is smaller than the second and the third diameters.

20. The balloon catheter of claim 14 wherein, when the balloon is inflated, the central portion of each said distal, intermediate and proximal sections of the balloon has a concave outer surface with respect to a central axis of the catheter, and the adjacent portions of each of said distal, intermediate and proximal sections has a convex outer surface with respect to the central axis of the catheter.

21. A dilation balloon catheter comprising:
   a catheter having a distal end, the catheter including at least one lumen extending therethrough;
   a balloon affixed about the distal end of the catheter, the balloon including a plurality of sections comprising a distal section, an intermediate section and a proximal section, said distal section, said intermediate section, and said proximal section each including a central portion having a waist located thereabout, wherein, when the balloon is inflated, the distal section has a maximum diameter smaller than a maximum diameter of the intermediate section, and the maximum diameter of the intermediate section is smaller than the maximum diameter of the proximal section;
   a wire guide comprising a superelastic alloy, the wire guide situated within the at least one lumen of the catheter and extending through the catheter and the balloon; and
   a system of indicia comprising a first indicium, a second indicium, and a third indicium, the system of indicia located on at least one of the wire guide and the balloon, the first indicium corresponding to the central portion of the proximal section, the second indicium corresponding to the central portion of the intermediate section, and the third indicium corresponding to the central portion of the distal section.

22. The balloon catheter of claim 20 wherein, when the balloon is inflated, the central portion of each said distal, intermediate and proximal sections of the balloon has a concave outer surface with respect to a central axis of the catheter, and the adjacent portions of each of said distal, intermediate and proximal sections has a convex outer surface with respect to the central axis of the catheter.

* * * * *